(12) United States Patent
Amano et al.

(10) Patent No.: US 8,144,938 B2
(45) Date of Patent: Mar. 27, 2012

(54) BIOLOGICAL INFORMATION ACQUISITION DEVICE, METHOD FOR ACQUIRING BIOLOGICAL INFORMATION, AND BIOMETRICS DEVICE

(75) Inventors: Kazuhiko Amano, Tokyo-to (JP); Koichi Shimizu, Sapporo (JP)

(73) Assignees: Seiko Epson Corporation, Tokyo (JP); Hokkaido University, Hokkaido (JP)

( * ) Notice: Subject to any disclaimer, the term of this patent is extended or adjusted under 35 U.S.C. 154(b) by 1093 days.

(21) Appl. No.: 11/748,732

(22) Filed: May 15, 2007

(65) Prior Publication Data

US 2007/0270666 A1    Nov. 22, 2007

(30) Foreign Application Priority Data

May 16, 2006 (JP) .................................. 2006-136997
Mar. 9, 2007 (JP) .................................. 2007-060309

(51) Int. Cl.
*G06K 9/00* (2006.01)

(52) U.S. Cl. ........ 382/115; 382/116; 382/117; 382/118; 382/124; 382/125

(58) Field of Classification Search .................. 382/115, 382/116, 117, 118, 124, 125
See application file for complete search history.

(56) References Cited

U.S. PATENT DOCUMENTS

| 6,301,375 B1 * | 10/2001 | Choi | 382/115 |
| 2003/0046228 A1 * | 3/2003 | Berney | 705/41 |
| 2006/0023218 A1 * | 2/2006 | Jung et al. | 356/419 |

FOREIGN PATENT DOCUMENTS

| JP | A 05-081414 | 4/1993 |
| JP | A 05-182005 | 7/1993 |
| JP | A 2000-242771 | 9/2000 |
| JP | A 2002-533848 | 10/2002 |
| JP | B2 3549795 | 4/2004 |
| WO | WO 00/39744 A1 | 7/2000 |

* cited by examiner

*Primary Examiner* — Mike Rahmjoo
(74) *Attorney, Agent, or Firm* — Oliff & Berridge, PLC (57) ABSTRACT

A biological information acquisition device that acquires information from a biological body by irradiating the biological body with light, the device comprises: a light source irradiating the biological body with light; a plurality of light receiving elements receiving one of passed light and reflected light from the biological body irradiated with light by the light source; and an inhomogeneous neutral density filter disposed on the plurality of light receiving elements and in a light path of one of passed light and reflected light. An optical transmittance of the inhomogeneous neutral density filter is set so that intensity of each light component received by light receiving elements is evened out as a whole.

9 Claims, 6 Drawing Sheets

BIOLOGICAL INFORMATION ACQUISITION DEVICE, METHOD FOR ACQUIRING BIOLOGICAL INFORMATION, AND BIOMETRICS DEVICE

BACKGROUND

1. Technical Field

Several aspects of the present invention relate to a biological information acquisition device, a method for acquiring biological information, and a biometrics device that utilize biological information.

2. Related Art

Recently, in order to authenticate an authorized user, biometrics has been introduced that utilizes the user's biological information such as fingerprints, irises, and vein patterns. For example, it is cited in Japanese Patent No. 3549795. For implementing the biometrics, various biological information acquisition devices are used.

Among the devices, one is known that is provided with a light source for light irradiation and a light receiving element for receiving light. The device irradiates a biological body with light from the light source and receives light from the biological body to convert it into an electrical signal, acquiring biological information.

In these days in which apparatuses, such as portable devices and personal computers, that need authentication are widely used in daily life, biological information acquisition devices with a large body and high power consumption are given the cold shoulder by users.

In contrast, improving the accuracy of acquired biological information is demanded since higher accuracy is required in authentication by increasing security awareness.

However, a problem arises in that the quality and accuracy of the acquired biological information get lowered since the dynamic range of irradiation light and received light is limited. Particularly, light sources and light receiving elements used in small biological information acquisition devices are strictly limited in their power consumption, driving method, and size, which makes it difficult to use ones having high performance in terms of the dynamic range or the like.

SUMMARY

An advantage of the invention is to provide a biological information acquisition device, a method for acquiring biological information, and a biometrics device that can easily achieve downsizing the devices as well as acquire biological information with high accuracy.

Accordingly, the invention provides the following aspects.

A biological information acquisition device that acquires information from a biological body by irradiating the biological body with light according to a first aspect of the invention includes: a light source irradiating the biological body with light; a plurality of light receiving elements receiving one of passed light and reflected light from the biological body irradiated with light by the light source; and an inhomogeneous neutral density filter disposed on the plurality of light receiving elements and in a light path of one of passed light and reflected light. An optical transmittance of the inhomogeneous neutral density filter is set so that intensity of each light component received by light receiving elements is evened out as a whole.

In the biological information acquisition device, intensity of the light component at each light receiving element can be equalized regardless of the position from the light source since intensity of the light component received by each light receiving element can be evened out as a whole.

Therefore, the quality of acquired biological information can be improved even if a dynamic range of light is small.

In the biological information acquisition device, it is preferable that a first optical transmittance of a far part from the light source be higher than a second optical transmittance of a near part from the light source in the inhomogeneous neutral density filter.

In the biological information acquisition device, the amount of passed light through the inhomogeneous neutral density filter can be equalized on entire surface of the filter, allowing light intensity to be equalized on each light receiving element regardless of the position from the light source.

The biological information acquisition device is preferably wearable on a human body.

Using the biological information acquisition device allows biological information to be utilized in various scenes, improving convenience.

A method for acquiring information of a biological body by irradiating the biological body with light according to a second aspect of the invention includes: irradiating the biological body with light by a light source; and receiving one of passed light and reflected light from the biological body irradiated with light by the light source, through an inhomogeneous neutral density filter disposed in a light path of passed light or reflected light, with a plurality of light receiving elements so as to even out intensity of each light component received by the plurality of light receiving elements as a whole.

In the method for acquiring biological information, intensity of the light component at each light receiving element can be equalized regardless of the position from the light source since intensity of the light component received by each light receiving element can be evened out as a whole.

Therefore, the quality of acquired biological information can be improved even if a dynamic range of light is small.

A biometrics device according to a third aspect of the invention includes: a biological information acquisition part to acquire information of a biological body by irradiating the biological body with light, and an authentication part to perform personal authentication based on acquired information by the biological information acquisition part. The biological information acquisition part includes: a light source irradiating the biological body with light; a plurality of light receiving elements receiving one of passed light and reflected light from the biological body irradiated with light by the light source; and an inhomogeneous neutral density filter disposed on the plurality of light receiving elements and in a light path of passed light or reflected light. The authentication part includes: a biological information memory to store acquired information by the biological information acquisition part in advance; and an authentication controller that outputs an acknowledge signal of completing authentication in a case where stored information by the biological information memory in advance and acquired information by the biological information acquisition part coincide based on a result of comparing both information. An optical transmittance of the inhomogeneous neutral density filter is set so that intensity of each light component received by light receiving elements is evened out as a whole.

In the biometrics device, intensity of the light component at each light receiving element can be equalized regardless of the position from the light source since intensity of the light component received by each light receiving element can be evened out as a whole.

Therefore, the quality of acquired biological information can be improved even if a dynamic range of light is small. As a result, highly accurate authentication can easily be achieved.

The biometrics device is preferably wearable on a human body.

The biometrics device can perform biometrics in various scenes, improving convenience.

BRIEF DESCRIPTION OF THE DRAWINGS

The invention will be described with reference to the accompanying drawings, wherein like numbers reference like elements.

DESCRIPTION OF EXEMPLARY EMBODIMENTS

First Embodiment

A biometrics device according to a first embodiment of the invention will be described with reference to accompanying drawings.

Figure 1:
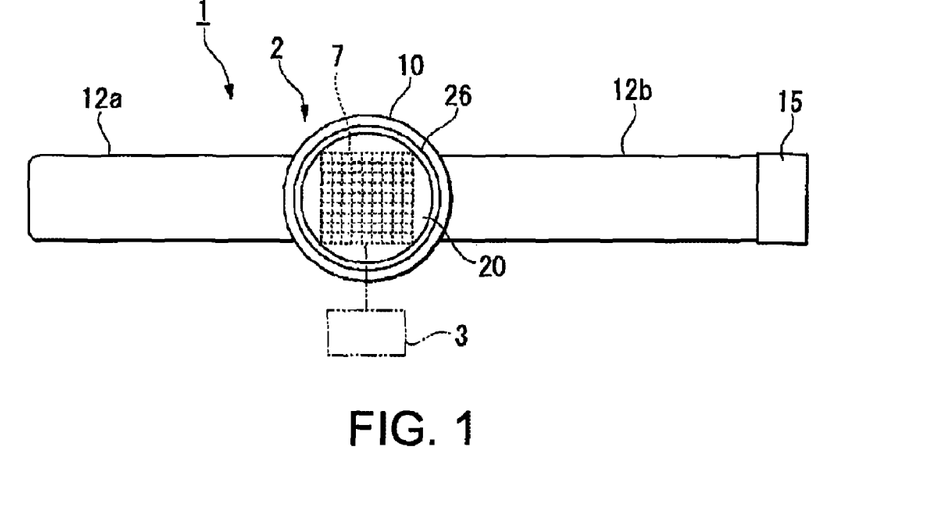
FIG. 1 is a plan view illustrating a biometrics device according to a first embodiment of the invention.

FIG. 1 illustrates a biometrics device 1 of the first embodiment.

The biometrics device 1 is provided with a circular base 10 formed in a circular plate shape. The circular base 10 is provided with bands 12a and 12b both of which extend in the same straight line. At the end of the band 12b, a locking part 15 for being locked at the end of the band 12a is provided.

Constructed as described above, the biometrics device 1 can be worn on a wrist by belting the wrist with the bands 12a and 12b, with the locking part 15 locked at the end of the band 12a.

The biometrics device 1 is also provided with a biological information acquisition part (biological information acquisition device) 2 to acquire a vein pattern of a biological body, and an authentication part 3 to perform personal authentication based on the vein pattern acquired by the biological information acquisition part 2.

The biological information acquisition part 2 is provided with a light receiver 7 to receive light, and an annular light source (light source) 26, which is formed in an annular shape and provided around the light receiver 7. The annular light source 26 is composed of LEDs, for example, while the light receiver 7 is composed of CCDs, for example. The light receiver 7 and the annular light source 26 are arranged on one of main surfaces of the circular base 10.

Figure 3:
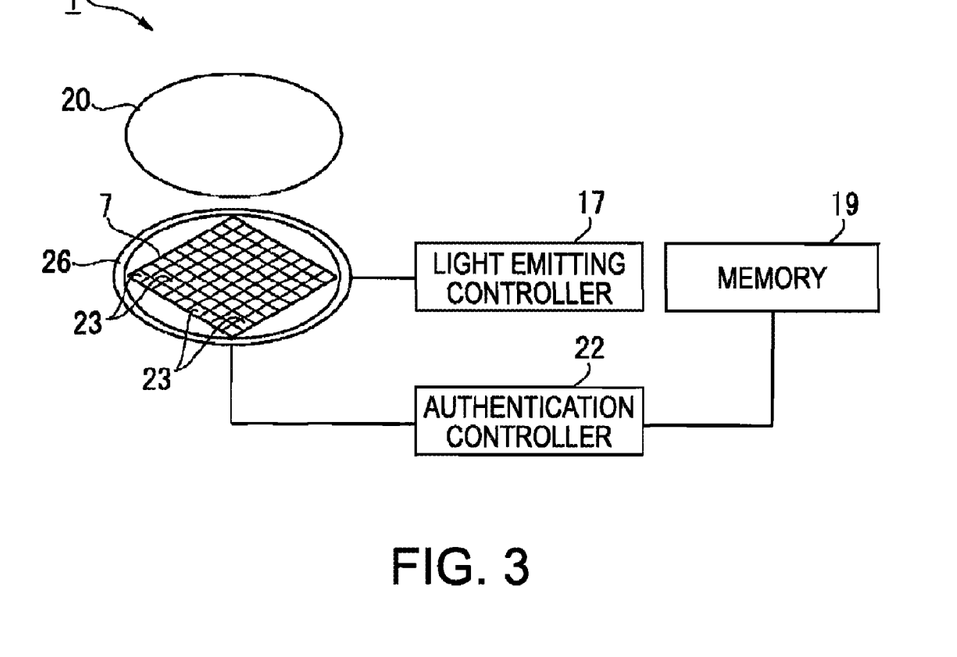
FIG. 3 is a block diagram illustrating functions of the biometrics device in FIG. 1.

As shown in FIG. 3, the annular light source 26 is electrically connected to a light emitting controller 17, emitting CW light as continuous waves by being controlled by the light emitting controller 17.

Figure 2:
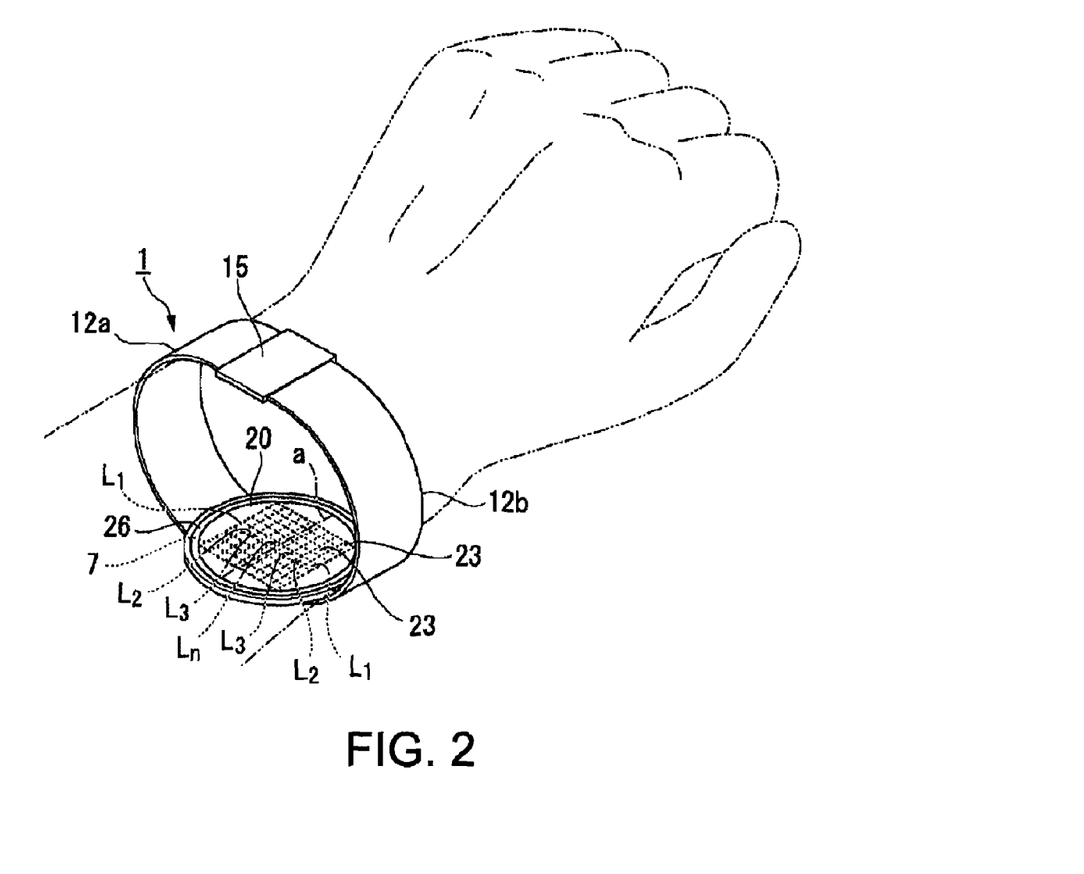
FIG. 2 is an explanatory view showing the biometrics device in FIG. 1 worn on a wrist.

The light receiver 7 is provided with a plurality of light receiving elements 23 arranged in an array, and a micro lens array (not shown) provided above the plurality of light receiving elements 23, in which array each lens corresponds to respective light receiving elements 23. As shown in FIG. 2, a light receiving element L1 is provided at the nearest position to the annular light source 26, followed by light receiving elements L2, L3, and so on, departing from the light receiving element L1, and a light receiving element Ln is provided at the farthest position from the annular light source 26 in the light receiving elements 23 when the biometrics device 1 is worn on a wrist. That is, L1 is the light receiving element disposed at the most outer part of the light receiver 7, while Ln is the light receiving element disposed at the central part of the light receiver As shown in FIG. 3, the light receiver 7 is electrically connected to an authentication controller 22 performing personal authentication, which controller 22 is electrically connected to a memory (biological information memory) 19.

The memory 19 memorizes an electrical signal from the light receiver 7 as vein pattern memory data.

The authentication controller 22 takes in an electrical signal as vein pattern acquisition data, and then compares it with vein pattern memory data stored in the memory 19 in advance. If both date coincide, recognizing the completion of authentication, the authentication controller 22 outputs an acknowledge signal to acknowledge the use of external devices.

In addition, an inhomogeneous neutral density filter 20 is disposed on the light receiver 7 (above the main surface of the circular base 10) in the embodiment. The inhomogeneous neutral density filter 20 is disposed in a light path through which CW light emitted from the annular light source 26 and reflected in the wrist passes in a state where the biometrics device 1 is worn on the wrist as shown in FIG. 2. That is, light reflected in the wrist passes through the inhomogeneous neutral density filter 20, reaching the light receiver 7.

The optical transmittance of the inhomogeneous neutral density filter is set so that intensity of each light component received by respective light receiving elements 23 is evened out as a whole. That is, it is set so that the amount of each light component passed through the inhomogeneous neutral density filter 20 is equalized in the entire surface of the inhomogeneous neutral density filter 20.

Figure 4:
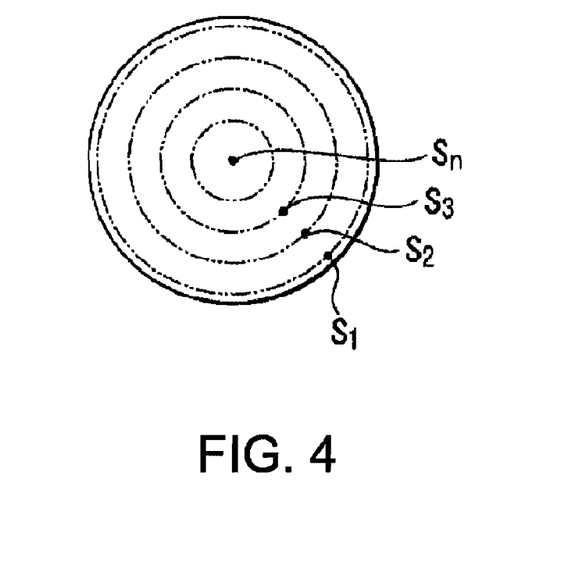
FIG. 4 is an enlarged plan view illustrating an inhomogeneous neutral density filter in FIG. 1.

Specifically, as shown in FIG. 4, the optical transmittance is set as the lowest level at a circular line SI located at the most outer part of the inhomogeneous neutral density filter 20, and becomes higher level as the position goes inwardly along the radial direction, such as circular lines S2 and S3, from the circular line S1. The optical transmittance in an area around a center point Sn is set as the highest level.

When the biometrics device 1 is worn on a wrist, the circular line S1 is disposed at the nearest position from the annular light source 26, followed by the circular lines S2, S3, ..., Sn inwardly along the radial direction. The area around the center point Sn is the farthest from the annular light source 26. That is, the optical transmittance of the inhomogeneous neutral density filter 20 is set as follows when the biometrics device 1 is worn on a wrist: the lowest level is set at the nearest position from the annular light source 26; as the position goes farther from the annular light source 26, the level becomes higher; and the highest level is set at the farthest position from the annular light source 26.

Next, the function of the biometrics device 1 will be described.

At first, an authorized user of an external apparatus registers his or her vein pattern. The user wears the biometrics device 1 on the wrist so that the light receiver 7 is positioned inside the wrist as shown in FIG. 2.

Then, the light emitting controller 17 outputs a driving signal to the annular light source 26. The annular light source 26 emits CW light. CW light is reflected in the wrist, and reflected light passes through the inhomogeneous neutral density filter 20, received by the light receiver 7.

In the related art, when the device is downsized, it is difficult to improve authentication accuracy since the accuracy of acquired biological information is low due to small dynamic range of reflected light.

The invention can improve the accuracy of acquired biological information as follows.

Light emitted from the annular light source 26 is reflected in the wrist, and reflected light reaches the inhomogeneous neutral density filter 20. On the inhomogeneous neutral density filter 20, light intensity shows the highest value at the circular line S1 the nearest position from the annular light source 26. Light intensity is gradually lowered as the position goes farther from the annular light source 26, showing the lowest value at the farthest position from the annular light source 26.

Figure 5:
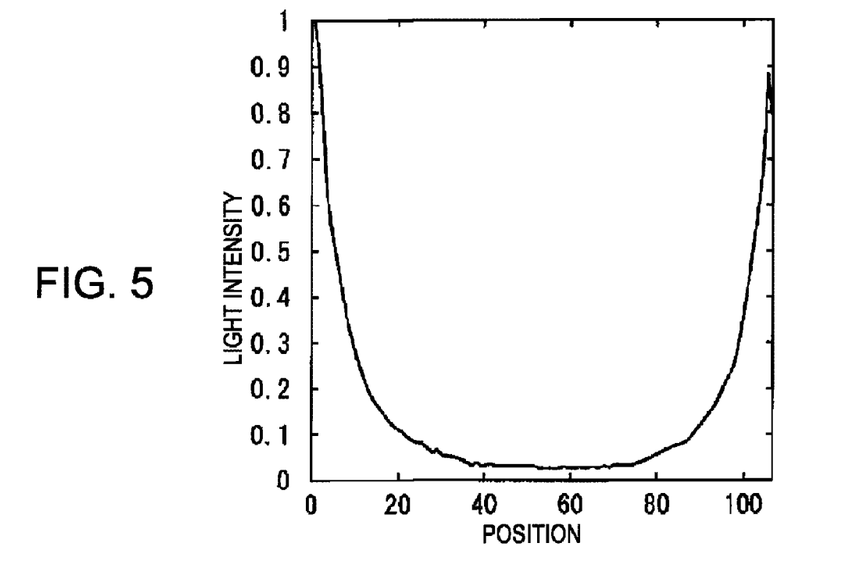
FIG. 5 is a graph showing light intensity distribution on line a in FIG. 2 when a homogeneous neutral density filter is set instead of the inhomogeneous neutral density filter in FIG. 1.

FIG. 5 is a graph showing light intensity distribution when a homogeneous neutral density filter is set instead of the inhomogeneous neutral density filter 20.

As shown in FIG. 5, light intensity shows the highest value at the most outer part of the filter, and is gradually lowered, as the position goes close to the center of the filter.

The optical transmittance of the inhomogeneous neutral density filter 20 of the embodiment is set so as to even out the light intensity distribution shown in FIG. 5. For example, light intensity is set as the inverse of the light intensity function shown in FIG. 5. That is, the optical transmittance of the inhomogeneous neutral density filter 20 is set as follows: the lowest level is set at the nearest position from the annular light source 26; the position goes farther from the annular light source 26, the level becomes higher; and the highest level is set at the farthest position from the annular light source 26.

Therefore, reflected light reached the circular line SI of the inhomogeneous neutral density filter 20 passes through it with most cut. The amount of light cut in the inhomogeneous neutral density filter 20 is progressively reduced as the position goes inwardly such as S2, S3, ..., Sn. At the center point Sn, light is least cut. As a result, intensity of reflected light through the inhomogeneous neutral density filter 20 is equalized in the entire surface of the inhomogeneous neutral density filter 20, resulting in light intensity distribution being evened out as a whole.

Figure 6:
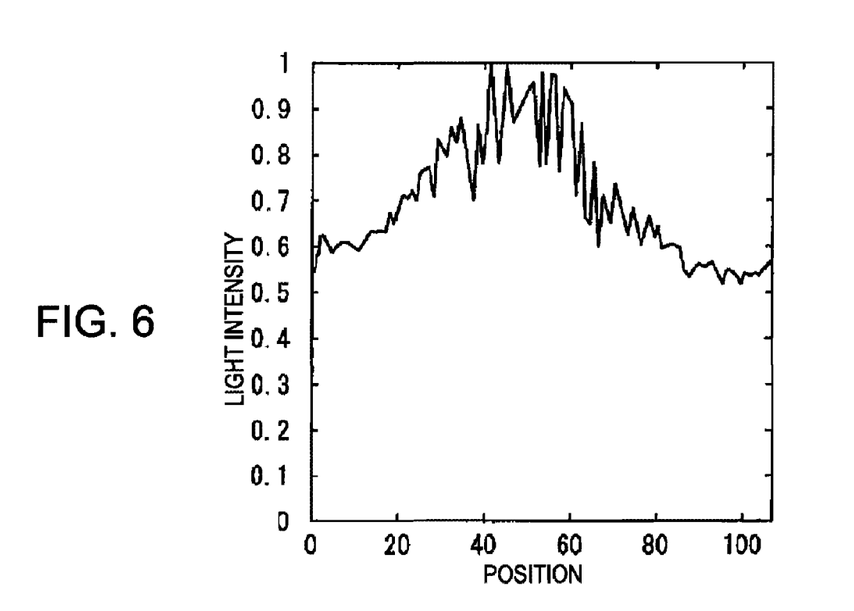
FIG. 6 is a graph showing light intensity distribution on line a in FIG. 2 when the inhomogeneous neutral density filter in FIG. 1 is set.

FIG. 6 is a graph showing light intensity distribution when the inhomogeneous neutral density filter 20 is set.

As shown in FIG. 6, the difference in light intensity between the most outer part and the center of the inhomogeneous neutral density filter 20 is markedly reduced. That is, it is understood that light intensity distribution is evened out as a whole.

As a result, the accuracy of acquired biological information can be improved even if the dynamic range is small.

Reflected light that is made to have even light intensity over the enter surface of the inhomogeneous neutral density filter 20 as described above is received by the light receiver 7. In this case, intensity of each light component received by the light receiving elements L1, L2, ..., Ln is equal. Then, the electrical signal output from the light receiver 7 is stored in the memory 19 as vein pattern memory data. As a result, vein pattern memory data of the authorized user is registered.

In the above measurement, a marker may be used for specifying the position to be measured. For, example, in acquiring a vein pattern at a wrist, as described later, the measurement may be conducted with a marker to indicate the position on the wrist to be measured.

Next, authentication will be described.

In authentication, the biometrics device 1 is worn on a wrist, and a vein pattern is acquired as described above. The authentication controller 22 takes in an electrical signal output from the light receiver 7 as vein pattern authentication data and compares it with vein pattern authentication data stored in the memory 19 in advance. If both date coincide, recognizing an authorized user and the completion of the authentication, the authentication controller 22 outputs an acknowledge signal to acknowledge the use of external devices. If both data do not coincide, the authentication controller 22 outputs a non-acknowledge signal as failed authentication.

According to the biometrics device 1 of the embodiment, intensity of the light component at each light receiving element 23 can be equalized regardless of the position from the annular light source 26 since intensity of the light component received by each light receiving element 23 can be evened out as a whole. Therefore, the quality of an acquired vein pattern can be improved even if the dynamic range is small. Improving authentication accuracy also can be realized.

In addition, since the biometrics device 1 can be worn on a wrist, biometrics can be performed in various scenes, improving convenience.

Further, a vein pattern can be rapidly and reliably acquired since the positions of the annular light source 26 and the light receiver 7 can be fixed for receiving reflected light from a biological body.

Second Embodiment

Next, a second embodiment according to the invention will be described.

Figure 7:
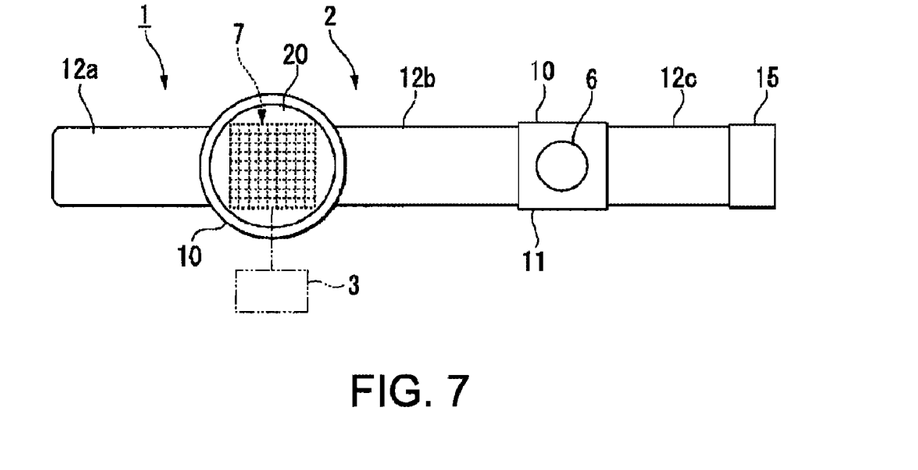
FIG. 7 is a plan view illustrating a biometrics device according to a second embodiment of the invention.
Figure 8:
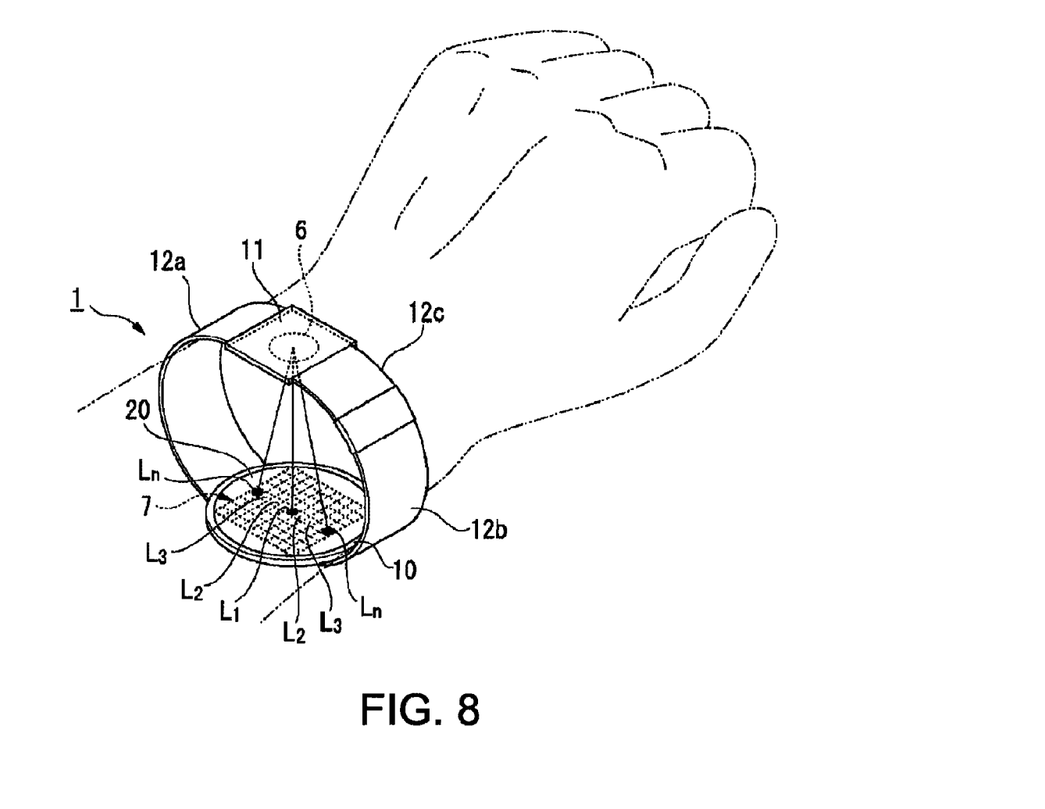
FIG. 8 is an explanatory view showing the biometrics device in FIG. 7 worn on a wrist.

FIGS. 7 and 8 illustrate the second embodiment.

In FIGS. 7 and 8, the same numeral is given to the same element shown in FIGS. 1 through 6.

The first and second embodiments have the same basic structure. Thus, only differences between them will be described.

As shown in FIG. 7, the biometric device 1 of the second embodiment is provided with the circular base 10, and a rectangular base 11 formed in a rectangular plate shape. The circular base 10 and the rectangular base 11 are connected with the band 12b.

The rectangular base 11 is provided with a band 12c, which extends in a direction opposite to the band 12b.

The rectangular base 11 is provided with a point-shaped light source (light source) 6 emitting irradiating light. The point-shaped light source 6 is composed of LEDs, for example.

Here, the circular base 10 is not provided with the annular light source 26.

In the embodiment, as shown in FIG. 8, the center point of the inhomogeneous neutral density filter 20 is disposed at the nearest position from the point-shaped light source 6, while the most outer part of the inhomogeneous neutral density filter 20 is disposed at the farthest position from the point-shaped light source 6 when the biometrics device 1 is worn on a wrist. Thus, the optical transmittance of the inhomogeneous neutral density filter 20 is set as the lowest level at the center point, becoming progressively higher as the position goes outwardly along in the radial direction, and the highest level at the most outer part.

In the above structure, when the point-shaped light source 6 irradiates a wrist with CW light, CW light passes through the wrist and passed light passes through the inhomogeneous neutral density filter 20, received by the light receiver 7. In this case, as the same as described above, light intensity distribution is evened out as a whole since the optical transmittance of the inhomogeneous neutral density filter 20 is set so as to be the lowest level at the center and the highest level at the most outer part.

Therefore, the same advantages of the first embodiment can be provided.

In addition, vertical distribution in a biological body can be observed without any limitation in a depth direction of the biological body since CW light is passed through the biological body and received.

Figure 9:
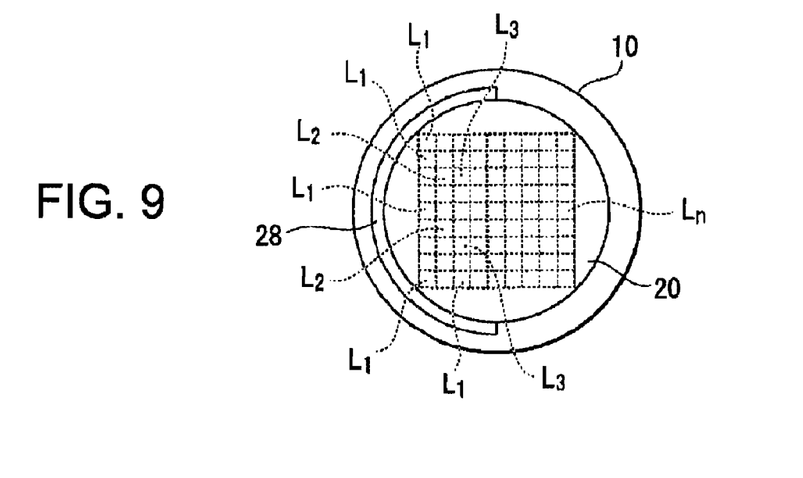
FIG. 9 is a plan view illustrating a modification example of a light source in FIG. 7.
Figure 10:
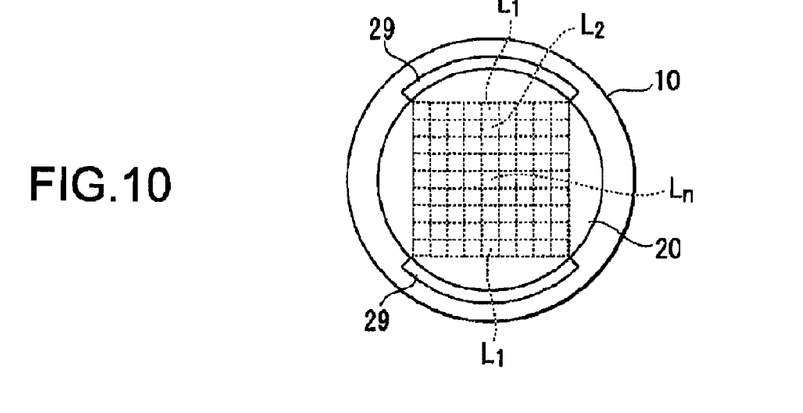
FIG. 10 is a plan view illustrating another modification example of the light source in FIG. 7.
Figure 11:
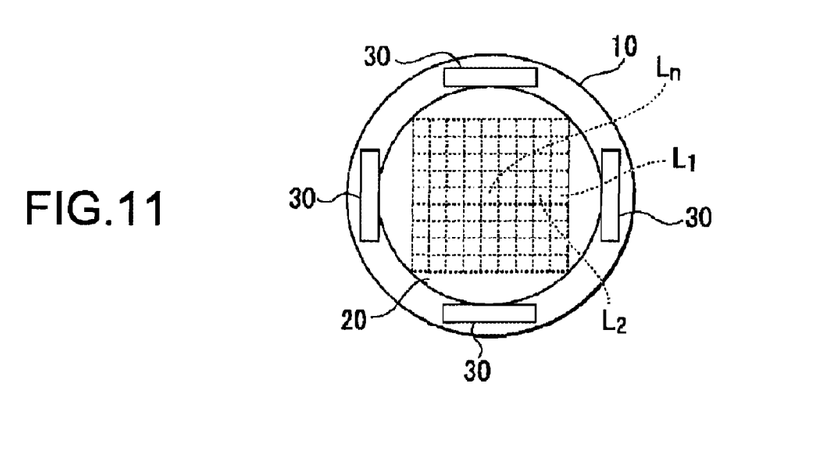
FIG. 11 is a plan view illustrating still another modification example of the light source in FIG. 7.

While the annular light source 26 is provided in the first embodiment, the invention is not limited to this. The shape and location of the light source can be changed accordingly. For example, as shown in FIG. 9, a half-annular light source (light source) 28 may be disposed half on the surround of the light receiver 7. As shown in FIG. 10, an arc-shaped light source (light source) 29 may be partially disposed on the surround of the light receiver 7. As shown in FIG. 11, a line-shaped light source (light source) 30 may be partially disposed on the surround of the light receiver 7. Even in these cases, it goes without saying that the optical transmittance of the inhomogeneous neutral density filter 20 is set so as to be lower level as the position goes closer to the light source, while higher as the position goes farther from the light source.

The light sources 26, 28, 29, and 30 may be disposed on the rectangular base 11 instead of the point-shaped light source 6 of the second embodiment.

Figure 12:
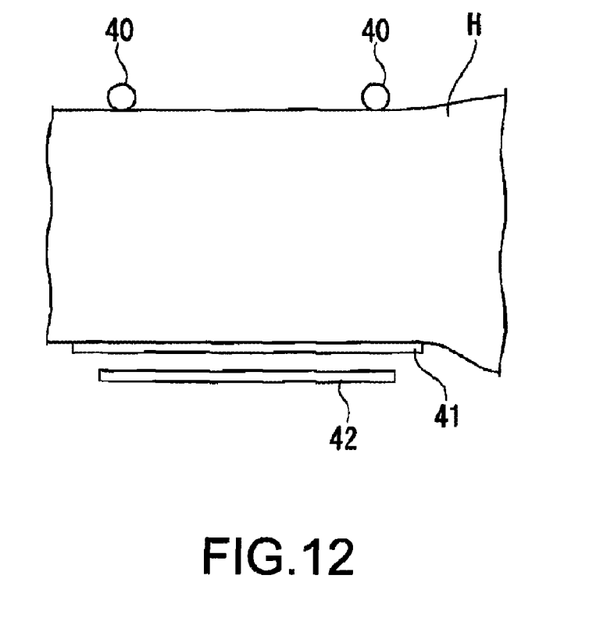
FIG. 12 is an explanatory view showing a modification example of a light source, a light receiving element, and an inhomogeneous neutral density filter in FIG. 1.

In addition, the light receiving element and the filter may be formed in a line shape. For example, as shown in FIG. 12, point-shaped light sources (light source) 40 are disposed on one side of a skin H, while a line-shaped light receiving element (light receiving element) 42 is disposed on the other side—opposite to the one side—of the skin H. Additionally, a line-shaped filter (inhomogeneous neutral density filter) 41 is disposed on the other side of the skin H and between the line-shaped light receiving element 42 and the skin H. It goes without saying that the optical transmittance of the line-shaped filter 41 is set so as to be lower level as the position goes closer to the spot-shaped light source 40 as described above.

The spot-shaped light source 40 may be disposed as single source at the position corresponding to the central part in the longitudinal direction of the line-shaped light receiving element 42. In order to reduce influence of heat from the spot-shaped light source 40, it is preferable that the spot-shaped light source 40 be respectively set at the positions corresponding to the both ends of the line-shaped light receiving element 42 in the longitudinal direction.

The spot-shaped light source 40 also can function as a discrete light source by controlling it to turn on and off, effective for processing pixel image or the like.

In addition, three-dimensional image can easily be provided with a simple structure by scanning with the line-shaped light receiving element 42 made to slide in a direction perpendicular to the longitudinal direction when image information is required.

Figure 13:
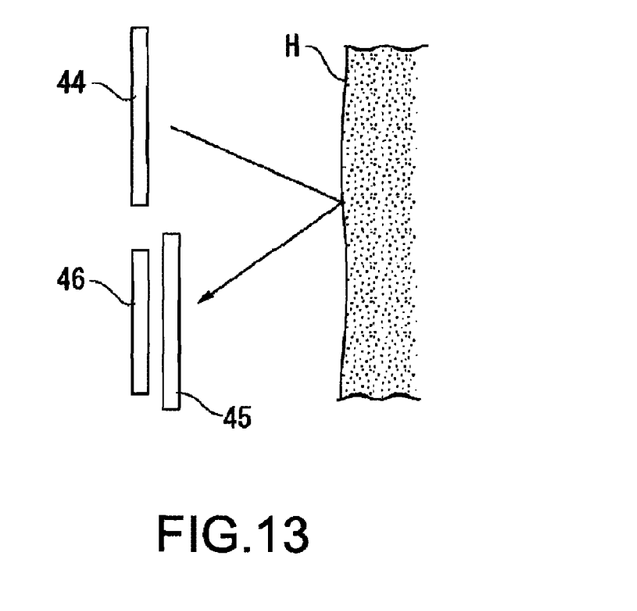
FIG. 13 is an explanatory view showing a modification example of a light source, a light receiving element, and an inhomogeneous neutral density filter in FIG. 12.

Further, as shown in FIG. 13, a line-shaped light source (light source) 44 is disposed above one side of the skin H, while a line-shaped light receiving element (light receiving element) 46 is disposed at a position that is in the vicinity of the line-shaped light source 44 and at which the line-shaped light receiving element 46 and the line-shaped light source 44 are not overlapped in their thickness direction. Additionally, a line-shaped filter 45 is disposed between the line-shaped light receiving element 46 and the skin H. It goes without saying that the optical transmittance of the line-shaped filter 45 is set so as to be lower level as the position goes closer to the line-shaped light source 44 as described above.

While a vein pattern is acquired as biological information in the first and second embodiments, the invention is not limited to this. Another biological information such as fingerprints and irises can be acquired.

The light source is not limited to being composed of LEDs, organic ELs and inorganic ELs also can be employed.

In single authentication, biological information acquisition may be performed in several times and then a light intensity result in each time may be accumulated. This procedure can lower noises and errors, allowing more accurate biological information to be acquired.

In addition, the output from the light emitting controller 17 may be controlled by measuring the light amount of passed light or reflected light and whether the light amount is within a predetermined range or not. That is if the light amount is small, the output from the light emitting controller 17 is made to increase. In contrast, if the light amount is large, a feedback is performed so as to make the output decrease. The output is controlled by current or voltage applied to the light source. This control allows energy saving to be achieved as well as biological information to be highly accurately and reliably acquired.

It should be understood that the technical scope of the invention is not limited to the above embodiments but applies to various kinds of modifications without departing from the spirit and scope of the invention.

For example, while the biometrics device is worn on a wrist in the above embodiments, any device configurations can be chosen in accordance with parts, such as palms, fingers, and ankles, used for authentication.

What is claimed is:

1. A biological information acquisition device that acquires information from a biological body by irradiating the biological body with light, the device comprising:
   a light source irradiating the biological body with light;
   a light receiver including a plurality of light receiving elements that are arranged in two dimensions, the plurality of light receiving elements receiving one of passed light and reflected light from the biological body irradiated with light by the light source; and
   an inhomogeneous neutral density filter disposed on the plurality of light receiving elements and on a light path of one of the passed light and the reflected light, wherein an optical transmittance of the inhomogeneous neutral density filter is set so that a plurality of intensities of each light component received by light receiving elements are evened out as a whole, wherein the light source is disposed around a perimeter of the light receiver.

2. The biological information acquisition device according to claim 1, wherein a first optical transmittance of a portion of the inhomogeneous neutral density filter farthest from the light source is higher than a second optical transmittance of a portion of the inhomogeneous neutral density filter nearest to the light source.

3. The biological information acquisition device according to claim 1, wherein the device is wearable on a human body.

4. The biological acquisition device according to claim 1, wherein the optical transmittance of the inhomogeneous neutral density filter is gradually reduced moving in a direction from a center of the inhomogeneous neutral density filter to an outer perimeter of the inhomogeneous neutral density filter.

5. The biological acquisition device according to claim 4, wherein the optical transmittance is lowest at an outer perimeter of the inhomogeneous neutral density filter and highest at the center of the inhomogeneous neutral density filter.

6. The biological acquisition device according to claim 1, wherein the two dimensions are a first direction and a second direction, the second direction being orthogonal to the first direction, and the receiving elements are arranged in an array having rows and columns in the first direction and the second direction.

7. A method for acquiring information of a biological body by irradiating the biological body with light, the method comprising:
   irradiating the biological body with light by a light source;
   receiving one of passed light and reflected light from the biological body irradiated with light by the light source, through an inhomogeneous neutral density filter disposed on a light path of one of the passed light and the reflected light, with a light receiver including a plurality of light receiving elements that are arranged in two dimensions so as to even out a plurality of intensities of each light component received by the plurality of light receiving elements as a whole, wherein
   the light source is disposed around a perimeter of the light receiver.

8. A biometrics device, comprising:
   a biological information acquisition part to acquire information of a biological body by irradiating the biological body with light, the biological information acquisition part including:
      a light source irradiating the biological body with light;
      a light receiver including a plurality of light receiving elements that are arranged in two dimensions, the plurality of light receiving elements receiving one of passed light and reflected light from the biological body irradiated with light by the light source; and
      an inhomogeneous neutral density filter disposed on the plurality of light receiving elements and on a light path of one of the passed light and the reflected light, wherein the light source is disposed around a perimeter of the light receiver; and
   an authentication part to perform personal authentication based on acquired information of the biological body by the biological information acquisition part, the authentication part including:
      a biological information memory to store acquired information of the biological body by the biological information acquisition part in advance; and
      an authentication controller that outputs an acknowledge signal of completing authentication in a case where stored information by the biological information memory in advance and acquired information by the biological information acquisition part coincide based on a result of comparing both information, wherein an optical transmittance of the inhomogeneous neutral density filter is set so that a plurality of intensities of each light component received by light receiving elements are evened out as a whole.

9. The biometrics device according to claim 8, wherein the device is wearable on a human body.

* * * * *